(12) United States Patent
Komuro et al.

(10) Patent No.: US 6,475,525 B1
(45) Date of Patent: Nov. 5, 2002

(54) ORAL PREPARATIONS CONTAINING FORSKOLIN DERIVATIVES AND PROCESS FOR PRODUCING PHARMACEUTICAL PREPARATIONS

(75) Inventors: Chikara Komuro, Tokyo (JP); Tomio Yahiro, Yono (JP); Hiroyuki Yoshida, Urawa (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/673,379

(22) PCT Filed: Apr. 30, 1998

(86) PCT No.: PCT/JP98/01973
§ 371 (c)(1),
(2), (4) Date: Oct. 16, 2000

(87) PCT Pub. No.: WO99/56743
PCT Pub. Date: Nov. 11, 1999

(30) Foreign Application Priority Data

Sep. 20, 1996 (JP) .............................................. 8-269168
Aug. 29, 1997 (JP) .............................................. 9-247533

(51) Int. Cl.$^7$ ............................ A61K 9/14; A61K 9/16; A61K 9/50
(52) U.S. Cl. ....................... 424/489; 424/400; 424/439; 424/451; 424/464; 424/490
(58) Field of Search .................................. 424/489, 490

(56) References Cited

FOREIGN PATENT DOCUMENTS

| JP | 63-10783 | 1/1988 |
| JP | 4-342526 | 11/1992 |
| JP | 10-147524 | 6/1998 |

OTHER PUBLICATIONS

Photocopy of periodic table.*
Concise Chemical and Technical Dictionary, Fourth Enlarged Edition, 1986, p. 54.*
Practical Medical Additives, Medical Additives Research Association, 1974, edited by Chemical Industries Co., Ltd., Tokyo, Japan, p. 258, lines 21–22, pp. 164–165 and pp. 23–28.
Sadasuke Okano, Introduction to Modern Pharmaceutics, edited by Nakodo, 1987, pp. 123–139.

* cited by examiner

Primary Examiner—Thurman K. Page
Assistant Examiner—Charesse Evans
(74) Attorney, Agent, or Firm—Nields & Lemack

(57) ABSTRACT

The pharmaceutical preparation comprising colforsin dapropate hydrochloride and an alkali metal halide is the oral preparation with excellent storage stability.

19 Claims, No Drawings

ORAL PREPARATIONS CONTAINING FORSKOLIN DERIVATIVES AND PROCESS FOR PRODUCING PHARMACEUTICAL PREPARATIONS

TECHNICAL FIELD

The present invention relates to a pharmaceutical preparation with good storage stability comprising a salt of a forskolin derivative which is useful for the treatment of chronic heart failure, etc., and a process for producing the pharmaceutical preparation.

BACKGROUND ART

It is known from JP-A-63-10783, etc., that the forskolin derivatives and their salts have a positive inotropic action, a vascular smooth muscle relaxing action and an adenylate cyclase activating action, etc. It is also known from JP-B-6-102625 that the forskolin derivatives and their salts are unstable to water. Further, JP-A-4-342526 discloses the granules and tablets in which lactose, crystalline cellulose, etc., have been compounded.

Since the forskolin derivatives and their salts, such as colforsin dapropate hydrochloride etc., are unstable to water, their preparations obtained from an ordinary wet granulation method using water have the defects that they are bad in storage stability and the degradation products increase with time. The preparations obtained from a dry granulation method using no water or a direct powder compaction method are relatively good in storage stability but have the problem in uniformity of content. In the preparations comprising a salt of a forskolin derivative, the content of the salt per preparation is small, so that a wet granulation method which hardly causes classification etc. is suited for ensuring content uniformity of the preparations. However, as mentioned above, it is impossible with an ordinary wet granulation method to obtain the preparations with good storage stability.

An object of the present invention is to provide an oral preparation containing a salt of a forskolin derivative, which preparation is cleared of the above defects and has excellent storage stability.

Another object of the present invention is to provide a process for producing the pharmaceutical preparation with excellent storage stability.

DISCLOSURE OF THE INVENTION

As a result of extensive studies for attaining the above-said objects, the present inventors found that by using an alkali metal halide, it is possible to obtain an oral preparation containing a salt of a forskolin derivative with excellent stability and to obtain a pharmaceutical preparation with excellent stability by a wet granulation method, and completed the present invention.

Thus, the present invention pertains to the following inventions 1) to 20):

1) An oral preparation characterized by comprising a salt of a forskolin derivative as a pharmaceutically active ingredient and an alkali metal halide;
2) An oral preparation according to 1) above, wherein the salt of a forskolin derivative is a salt of a forskolin derivative represented by the following formula (1):

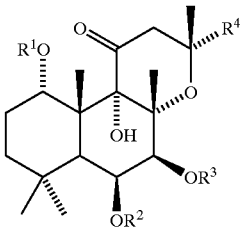

wherein $R^1$ is a hydrogen atom; $R^4$ is a vinyl group, an ethyl group or a cyclopropyl group; and one of $R^2$ and $R^3$ represents a partial structural formula —CO(CH$_2$)mNR$^5$R$^6$ wherein $R^5$ and $R^6$ are a hydrogen atom or a lower alkyl group or they are combined together to represent a lower alkylene group which may contain an oxygen atom or a nitrogen atom in the bonding chain, and m is an integer of 1 to 5 and the other represents a hydrogen atom or a partial structural formula —CO(CH$_2$)nX wherein X is a hydrogen atom or a group represented by the formula —NR$^7$R$^8$ wherein $R^7$ and $R^8$ are a hydrogen atom or a lower alkyl group or they are combined to represent a lower alkylene group which may contain an oxygen atom or a nitrogen atom in the bonding chain, and n is an integer of 1 to 5;

3) An oral preparation according to 1) or 2) above, wherein the salt of a forskolin derivative is colforsin dapropate hydrochloride (a hydrochloride of 6-(3-dimethylaminopropionyl)forskolin);

4) An oral preparation according to 1), 2) or 3) above, wherein the alkali metal halide is sodium chloride or potassium chloride;

5) An oral preparation according to 1), 2), 3) or 4) above, wherein an alkali metal halide is contained in an amount of 0.01 to 26 parts by weight per one part by weight of a salt of a forskolin derivative;

6) An oral preparation according to 1), 2), 3) or 4) above, wherein an alkali metal halide is contained in an amount of 0.25 to 10 parts by weight per one part by weight of a salt of a forskolin derivative;

7) An oral preparation according to 1), 2), 3), 4), 5) or 6) above, wherein a pharmaceutical adjuvant or adjuvants are contained in an amount of 10 to 500 parts by weight per one part by weight of a salt of a forskolin derivative;

8) An oral preparation comprising:
   a salt of a forskolin derivative as a pharmaceutically active ingredient: 0.01–26 wt % an alkali metal halide: 0.05–22 wt %
   a pharmaceutical adjuvant or adjuvants: 52–99.9 wt % based on the whole preparation;

9) An oral preparation comprising:
   a salt of a forskolin derivative as a pharmaceutically active ingredient: 0.03–13 wt %
   sodium chloride or potassium chloride: 0.25–11 wt %
   a pharmaceutical adjuvant or adjuvants: 76–99.7 wt % based on the whole preparation;

10) An oral preparation according to 8) or 9) above, wherein the salt of a forskolin derivative is colforsin dapropate hydrochloride;

11) A process for producing a pharmaceutical preparation characterized by using an aqueous solution of an alkali metal halide in wet-granulating a mixture of a pharmaceutically active ingredient and a pharmaceutical adjuvant or adjuvants;

12) A process for producing a pharmaceutical preparation characterized by mixing a pharmaceutically active ingredient, a solid alkali metal halide and a pharmaceutical adjuvant or adjuvants, and wet-granulating the mixture;

13) The process according to 11) or 12) above, wherein the pharmaceutically active ingredient is a salt of a forskolin derivative;

14) The process according to 11) or 12) above, wherein the pharmaceutically active ingredient is colforsin dapropate hydrochloride;

15) The process according to I11), 12), 13) or 14) above, wherein the alkali metal halide is sodium chloride or potassium chloride;

16) The process according to 11), 12), 13), 14) or 15) above, wherein a pharmaceutical adjuvant or adjuvants and an alkali metal halide are used in amounts of 10 to 500 parts by weight and 0.01 to 26 parts by weight, respectively, per one part by weight of the pharmaceutically active 17) The process according to 11), 12), 13), 14) or 15) above, wherein a pharmaceutical adjuvant or adjuvants and an alkali metal halide are used in amounts of 10 to 500 parts by weight and 0.25 to 10 parts by weight, respectively, per one part by weight of the pharmaceutically active 18) The process according to any one of 11) and 13) to 17) above, wherein the concentration of the alkali metal halide in its aqueous solution is from 1% by weight to the concentration of saturated solution;

19) The process according to any one or 11) and 13) to 17) above, wherein the concentration of the alkali metal halide in its aqueous solution is from 5% by weight to the concentration of saturated solution;

20) The process according to any one of 12) to 17) above, wherein the solid alkali metal halide is powder type.

BEST MODE FOR CARRYING OUT THE INVENTION

The present invention will be described in detail below.

As a salt of a forskolin derivative, it is possible to use any of those which can serve as a pharmaceutically active ingredient, but preferably the forskolin derivatives represented by the above-shown formula (1) are used. As the lower alkyl group in the formula (1), the alkyl groups having 1 to 4 carbon atoms such as methyl group, ethyl group, propyl group, butyl group, etc. may be exemplified. As the lower alkylene group which may contain an oxygen atom or a nitrogen atom in the chain, those of 3 to 5 carbon atoms such as —$(CH_2)_3$—, —$(CH_2)_4$—, —$(CH_2)_5$—, —$(CH_2)_2$—NH—$(CH_2)_2$—, —$(CH_2)_2$—O—$(CH_2)_2$—, etc. may be exemplified.

As the groups of —$CO(CH_2)mNR^5R^6$, for example, dimethylaminoacetyl group, diethylaminoacetyl group, diethylaminopropionyl group, butylaminoacetyl group, dimethylaminopropionyl group, dimethylaminobutylyl group, pyrrolidinobutylyl group, pyrrolidinoacetyl group, piperadinoacetyl group, morpholinoacetyl group, etc. may be exemplified.

As the groups of —$CO(CH_2)n$—X, for example, acetyl group, propionyl group, butylyl group and various types of aminoacyl groups such as mentioned above may be exemplified.

Preferred among the compounds of the formula (1) are those of the formula wherein $R^2$ is —$CO(CH_2)mNR^5R^6$ wherein m is 1 to 4, and $R^5$ and $R^6$ are both a lower alkyl group, and $R^3$ is an acetyl group.

As the salts of the forskolin derivatives, inorganic acid salts such as hydrochlorides, hydrobromides, sulfates, phosphates, etc., and organic acid salts such as formates, acetates, fumarates, maleates, citrates, tartarates, lactates, methanesulfonates, etc., may be exemplified. Any of the pharmacologically acceptable salts may be used, and hydrochlorides are especially preferred.

Of the salts of forskolin derivatives, colforsin dapropate hydrochloride may be especially preferably exemplified.

The alkali metal halide used in the present invention is not specifically defined; it is possible to use any one those alkali metal halides which are usable as a pharmaceutical adjuvant, the typical examples of which are sodium chloride, potassium chloride, sodium bromide, potassium bromide, etc. These alkali metal halides can be used either singly or as a mixture of two or more of them. Sodium chloride or potassium chloride is preferably used.

The amount of the alkali metal halide is usually 0.01 parts by weight or more, preferably 0.25 parts by weight or more, per one part by weight of a salt of a forskolin derivative. Its upper limit is not specifically defined, but from the viewpoint of practical application, the upper limit is usually 26 parts by weight, preferably 10 parts by weight. Thus, the amount of the alkali metal halide is normally 0.01 to 26 parts by. weight, preferably 0.25 to 10 parts by weight per one part by weight of colforsin hydrochloride.

The oral preparation according to the present invention is not specifically restricted in the form; it may be offered, for example, in the form of granules, capsules, tablets and such. In the production of these preparations, it is possible to add, besides a salt of a forskolin derivative and an alkali metal halide, the pharmaceutical adjuvants which are usually used for the pharmaceutical preparations, such as excipient, binder, disintegrator, lubricant, etc. These adjuvants may be used singly or in combination of two or more. The amount of such adjuvant(s) to be added, although variable depending on the desired concentration of a salt of a forskolin derivative in the preparation, is usually about 10 to 500 parts by weight per one part by weight of the forskolin derivative salt.

As the excipient, monosaccharides such as dextrose and fructose, oligosaccharides such as lactose, sucrose, maltose, etc., polysaccharides such as corn starch, hydroxypropyl starch, etc., and sugar alcohols such as mannitol, xylitol, sorbitol, etc. may be exemplified.

As the binder, water-soluble cellulose derivatives such as hydroxypropyl cellulose, methyl cellulose, hydroxypropyl methylcellulose, etc. may be exemplified.

As the disintegrator, water-swollen cellulose derivatives such as carboxymethyl cellulose etc. may be exemplified.

As the lubricant, stearic acid and stearates such as magnesium stearate etc. may be exemplified.

As the adjuvants other than those mentioned above, any of the commonly used ones such as coating base, flavors and perfumes, colorant, etc., may be used in conformity to the preparation form. The amount (total amount) of the pharmaceutical adjuvants to be blended can not be decided unequivocally as it may differ depending on the type of the preparation and the type of the adjuvant(s) used, but it is usually 52 to 99.9% by weight, preferably 76 to 99.7% by weight based on the whole preparation.

The ratios of a salt of forskolin derivative, an alkali metal halide and other pharmaceutical adjuvants such as excipient, binder, disintegrator, lubricant, etc., to the whole preparation are usually as follows:

Salt of a Forskolin Derivative:

0.01% by weight or more, preferably 0.03% by weight or more; the upper limit being 26% by weight, preferably 13% by weight.

Alkal Metal Halide:

0.05% by weight or more, preferably 0.25% by weight or more; the upper limit being 22% by weight, preferably 11% by weight.

Pharmaceutical Adjuvants:

52% by weight or more, preferably 76% by weight or more; the upper limit being 99.9% by weight, preferably 99.7% by weight.

In producing the oral preparations of the present invention, the component materials mentioned above are usually formulated into granules by a wet granulation method. They may be formulated into tablets, capsules or granules as desired. It is particularly desirable to obtain these preparations according to the process described in 11) or 12) above.

Next, the processes for producing the pharmaceutical preparations of the present invention described in 11) and 12) above are explained. These processes can be used in producing various types of pharmaceutical preparations, for example, in producing the oral preparations mentioned above. The wet granulation method is a method in which the powdery starting material is wetted with a liquid and granulated by making use of its adhesive force. In the process of 11), an aqueous solution of an alkali metal halide is used as the said liquid. That is, a pharmaceutically active ingredient, pharmaceutical adjuvants and an aqueous solution of an alkali metal halide are mixed and granulated, then the mixture may be formulated into tablets, capsules or granules as desired. For instance, the pharmaceutically active ingredient and pharmaceutical adjuvants are mixed uniformly, then an aqueous solution of an alkali metal halide is supplied as a binding liquid, the mixture is granulated, dried and if necessary screened to form the granules. As the binding liquid, an aqueous solution of sodium chloride, potassium chloride, sodium bromide, potassium bromide or the like can be used, but an aqueous solution of sodium chloride and/or potassium chloride is preferred. The concentration of the alkali metal halide in its aqueous solution is generally 1% by weight or above, preferably 5% by weight or above, the upper limit thereof being the saturated solubility of the alkali metal halide used, preferably not higher than 30%.

An aqueous solution of an alkali metal halide is usually used in an amount of 5 to 40 parts by weight per 100 parts by combined weight of the pharmaceutically active ingredient and pharmaceutical adjuvants.

In the process of 12), a pharmaceutically active ingredient, pharmaceutical adjuvants and a solid alkali metal halide (preferably powder type) are mixed, and by using water as a binding liquid, the mixture is granulated, dried and if necessary screened to obtain the objective granules. The mixture may be formulated into tablets, capsules or granules as desired to obtain a pharmaceutical preparation.

The oral preparation of the present invention has excellent storage stability, and the pharmaceutical preparation producing processes of the present invention are capable of producing the pharmaceutical preparation with excellent storage stability.

In the following, the present invention is described in further detail by showing its examples, but it is to be understood that the scope of the present invention is not restricted by these examples. In the following Examples, all "%" and "parts" are by weight unless otherwise noted.

EXAMPLE 1

1.18 parts of colforsin hydrochloride, 104.59 parts of lactose, 7.05 parts of carboxymethyl cellulose and 3.52 parts of hydroxypropyl cellulose were mixed, and the mixture was wet granulated with 12.24 parts of a 25 wt % aqueous solution of sodium chloride and then dried at 50° C. After drying, the granulated product was screened, then 0.6 parts of magnesium stearate was mixed and the mixture was compression molded into tablets, thus obtaining a product of the present invention.

The composition of Example 1 is shown in Table 1.

TABLE 1

Composition of tablet of Example 1

| Starting materials | Composition (%) |
|---|---|
| Colforsin hydrochloride | 0.98 |
| Lactose | 87.16 |
| Carboxymethyl cellulose | 5.88 |
| Hydroxypropyl cellulose | 2.93 |
| Sodium chloride | 2.55 |
| Magnesium stearate | 0.50 |

EXAMPLE 2

1.16 parts of colforsin hydrochloride, 103.26 parts of lactose, 6.96 parts of carboxymethyl cellulose and 3.48 parts of hydroxypropyl cellulose were mixed, and the mixture was wet granulated with 18.16 parts of a 25 wt % aqueous solution of sodium chloride and then dried at 50° C. After drying, the produced granules were screened, then 0.6 parts of magnesium stearate was mixed and the mixture was compression molded into tablets, thus obtaining a product of the present invention.

The composition of Example 2 is shown in Table 2.

TABLE 2

Composition of tablet of Example 2

| Starting materials | Composition (%) |
|---|---|
| Colforsin hydrochloride | 0.97 |
| Lactose | 86.05 |
| Carboxymethyl cellulose | 5.80 |
| Hydroxypropyl cellulose | 2.90 |
| Sodium chloride | 3.78 |
| Magnesium stearate | 0.50 |

EXAMPLE 3

1.15 parts of colforsin hydrochloride, 101.98 parts of lactose, 6.87 parts of carboxymethyl cellulose and 3.44 parts of hydroxypropyl cellulose were mixed, and the mixture was wet granulated with 23.84 parts of a 25 wt % aqueous solution of sodium chloride and then dried at 50° C. After drying, the produced granules were screened, then 0.6 parts of magnesium stearate was mixed and the mixture was compression molded into tablets, thereby obtaining a product of the present invention.

The composition of Example 3 is shown in Table 3.

TABLE 3

Composition of tablet of Example 3

| Starting materials | Composition (%) |
|---|---|
| Colforsin hydrochloride | 0.96 |
| Lactose | 84.98 |
| Carboxymethyl cellulose | 5.73 |

TABLE 3-continued

Composition of tablet of Example 3

| Starting materials | Composition (%) |
|---|---|
| Hydroxypropyl cellulose | 2.87 |
| Sodium chloride | 4.97 |
| Magnesium stearate | 0.50 |

EXAMPLE 4

1.0 part of colforsin hydrochloride, 216.8 parts of lactose, 14.4 parts of carboxymethyl cellulose and 7.2 parts of hydroxypropyl cellulose were mixed, and the mixture was wet granulated with 33.6 parts of a 25 wt % aqueous solution of sodium chloride and then dried at 50° C. After drying, the produced granules were screened, then 0.6 parts of magnesium stearate was mixed and the mixture was compression molded into tablets, thereby obtaining a product of the present invention.

The composition of Example 4 is shown in Table 4.

TABLE 4

Composition of tablet of Example 4

| Starting materials | Composition (%) |
|---|---|
| Colforsin hydrochloride | 0.40 |
| Lactose | 87.28 |
| Carboxymethyl cellulose | 5.80 |
| Hydroxypropyl cellulose | 2.90 |
| Sodium chloride | 3.38 |
| Magnesium stearate | 0.24 |

EXAMPLE 5

1.0 part of colforsin hydrochloride, 107.9 parts of lactose, 7.2 parts of carboxymethyl cellulose and 3.6 parts of hydroxypropyl cellulose were mixed, and the mixture was wet granulated with 16.8 parts of a 25 wt % aqueous solution of sodium chloride and then dried at 50° C. After drying, the granules were screened, then 0.3 parts of magnesium stearate was mixed and the mixture was compression molded into tablets, thereby obtaining a product of the present invention.

The composition of Example 5 is shown in Table 5.

TABLE 5

Composition of tablet of Example 5

| Starting materials | Composition (%) |
|---|---|
| Colforsin hydrochloride | 0.81 |
| Lactose | 86.88 |
| Carboxymethyl cellulose | 5.80 |
| Hydroxypropyl cellulose | 2.90 |
| Sodium chloride | 3.38 |
| Magnesium stearate | 0.24 |

EXAMPLE 6

1.0 part of colforsin hydrochloride, 103.44 parts of lactose, 8.27 parts of carboxymethyl cellulose and 6.99 parts of hydroxypropyl cellulose were mixed, and the mixture was wet granulated with 16.8 parts of a 10 wt % aqueous solution of sodium chloride and then dried at 50° C. After drying, the granules were screened, then 0.3 parts of magnesium stearate was mixed and the mixture was compression molded into tablets, thereby obtaining a product of the present invention.

The composition of Example 6 is shown in Table 6.

TABLE 6

Composition of tablet of Example 6

| Starting materials | Composition (%) |
|---|---|
| Colforsin hydrochloride | 0.82 |
| Lactose | 85.01 |
| Carboxymethyl cellulose | 6.80 |
| Hydroxypropyl cellulose | 5.74 |
| Sodium chloride | 1.38 |
| Magnesium stearate | 0.25 |

EXAMPLE 7

1.0 part of colforsin hydrochloride, 89.3 parts of lactose, 2.1 parts of carboxymethyl cellulose and 6.0 parts of hydroxypropyl cellulose were mixed, and the mixture was wet granulated with 14 parts of a 10 wt % 3aqueous solution of sodium chloride and then dried at 50° C. After drying, the granules were screened, then 0.2 parts of magnesium stearate was mixed and the mixture was compression molded into tablets, thereby obtaining a product of the present invention.

The composition of Example 7 is shown in Table 7.

TABLE 7

Composition of tablet of Example 7

| Starting materials | Composition (%) |
|---|---|
| Colforsin hydrochloride | 1.0 |
| Lactose | 89.3 |
| Carboxymethyl cellulose | 2.1 |
| Hydroxypropyl cellulose | 6.0 |
| Sodium chloride | 1.4 |
| Magnesium stearate | 0.2 |

EXAMPLE 8

2.0 parts of colforsin hydrochloride, 88.4 parts of lactose, 2.1 parts of carboxymethyl cellulose and 5.9 parts of hydroxypropyl cellulose were mixed, and the mixture was wet granulated with 14 parts of a 10 wt % aqueous solution of sodium chloride and then dried at 50° C. After drying, the granules were screened, then 0.2 parts of magnesium stearate was mixed and the mixture was compression molded into tablets, thereby obtaining a product of the present invention.

The composition of Example 8 is shown in Table 8.

TABLE 8

Composition of tablet of Example 8

| Starting materials | Composition (%) |
|---|---|
| Colforsin hydrochloride | 2.0 |
| Lactose | 88.4 |
| Carboxymethyl cellulose | 2.1 |
| Hydroxypropyl cellulose | 5.9 |
| Sodium chloride | 1.4 |
| Magnesium stearate | 0.2 |

EXAMPLE 9

1.0 part of colforsin hydrochloride, 89.3 parts of lactose, 2.1 parts of carboxymethyl cellulose and 6.0 parts of hydroxypropyl cellulose were mixed, and the mixture was wet granulated with 14 parts of a 10 wt % aqueous solution of sodium chloride and then dried at 50° C. After drying, the granules were screened, 0.2 parts of magnesium stearate was mixed and the mixture was compression molded. A film coating liquid prepared by dissolving and suspending 2.28 parts of hydroxypropyl methylcellulose, 0.15 parts of titanium oxide and 0.57 parts of propylene glycol in a water/ethanol mixed solution was sprayed on the compression molded product and dried to produce the film-coated tablets.

The composition of Example 9 is shown in Table 9.

TABLE 9

Composition of tablet of Example 9

| Starting materials | Composition (%) |
| --- | --- |
| Colforsin hydrochloride | 0.97 |
| Lactose | 86.70 |
| Carboxymethyl cellulose | 2.04 |
| Hydroxypropyl cellulose | 5.83 |
| Sodium chloride | 1.36 |
| Magnesium stearate | 0.19 |
| Hydroxypropyl methylcellulose | 2.21 |
| Titanium oxide | 0.15 |
| Propylene glycol | 0.55 |

EXAMPLE 10

2.0 parts of colforsin hydrochloride, 89.3 parts of lactose, 2.1 parts of carboxymethyl cellulose and 6.0 parts of hydroxypropyl cellulose were mixed, and the mixture was wet granulated with 14 parts of a 10 wt % aqueous solution of sodium chloride and then dried at 50° C. After drying, the granules were screened, then 0.2 parts of magnesium stearate was mixed and the mixture was compression molded. A film coating liquid prepared by dissolving and suspending 2.28 parts of hydroxypropyl methylcellulose, 0.15 parts of titanium oxide and 0.57 parts of propylene glycol in a water/ethanol mixed solution was sprayed on the compression molded product and dried to produce the film coated tablets.

The composition of Example 10 is shown in Table 10.

TABLE 10

Composition of tablet of Example 10

| Starting materials | Composition (%) |
| --- | --- |
| Colforsin hydrochloride | 1.92 |
| Lactose | 85.87 |
| Carboxymethyl cellulose | 2.02 |
| Hydroxypropyl cellulose | 5.77 |
| Sodium chloride | 1.35 |
| Magnesium stearate | 0.19 |
| Hydroxypropyl methylcellulose | 2.19 |
| Titanium oxide | 0.14 |
| Propylene glycol | 0.55 |

EXAMPLE 11

1.0 part of colforsin hydrochloride, 89.3 parts of lactose, 2.1 parts of carboxymethyl cellulose, 6.0 parts of hydroxypropyl cellulose and 1.4 parts of sodium chloride were mixed, and the mixture was wet granulated with 14.0 parts of water and then dried at 50° C. After drying, the granules were screened, then 0.2 parts of magnesium stearate was mixed and the mixture was compression molded into tablets, thereby obtaining a product of the present invention. The composition is shown in Table 11.

TABLE 11

Composition of tablet of Example 11

| Starting materials | Composition (%) |
| --- | --- |
| Colforsin hydrochloride | 1.0 |
| Lactose | 89.3 |
| Carboxymethyl cellulose | 2.1 |
| Hydroxypropyl cellulose | 6.0 |
| Sodium chloride | 1.4 |
| Magnesium stearate | 0.2 |

The action and effect of the preparations of the present invention are explained specifically by the Test Examples.

TEST EXAMPLE 1

Storage Stability Test (1)

1. Specimens

Control: Tablets obtained by a wet granulation method without using any halogenated alkali metal.

Present invention: Tablets of Examples 1 to 3.

The above specimens were produced in the manner described below.

Control: colforsin dapropate hydrochloride (hereinafter called "colforsin hydrochloride"), lactose, carboxymethyl cellulose and hydroxypropyl cellulose were uniformly mixed, and the mixture was wet granulated by adding 15% by weight of water, then dried and, after screened, compression molded with magnesium stearate to make the tablets.

| The control composition is shown below. | |
| --- | --- |
| Starting materials | Composition (wt %) |
| Colforsin hydrochloride | 2 |
| Lactose | 88 |
| Carboxymethyl cellulose | 6 |
| Hydroxypropyl cellulose | 3 |
| Magnesium stearate | 1 |

Present invention: As the tablets of the present invention, those of Examples 1 to 3 were used.

2. Test Method and Test Results

Each specimen was kept under a condition of 65° C. and 75% relative humidity for 10 days, and as a purity test, the produced amounts of the deacetyl compound and the acryloyl compound which are the decomposition products of colforsin hydrochloride were determined. The produced amounts were measured as the ratios of the area of deacetyl compound and acryloyl compound to the total area of colforsin hydrochloride, deacetyl compound and acryloyl compound by a liquid chromatographic method. The results are shown in Table 12.

TABLE 12

| | Storage stability | | | |
| --- | --- | --- | --- | --- |
| | Initial | | After 10 days of storage | |
| Specimen | Deacetyl compound | Acryloly compound | Deacetyl compound | Acryloly compound |
| Control | 0.28% | 0.00% | 2.48% | 0.45% |
| Example 1 | 0.24% | 0.00% | 0.25% | 0.00% |
| Example 2 | 0.28% | 0.05% | 0.24% | 0.00% |
| Example 3 | 0.25% | 0.00% | 0.25% | 0.00% |

TEST EXAMPLE 2

Storage Stability Test (2)

1. Specimens

Control: Same as used in Test Example 1. Present invention: Tablets of Examples 4–6 and 11

2. Test Method and Test Results

Each specimen was kept under a condition of 65° C. for 21 days (28 days for the specimen of Example 11), and as a purity test, the produced amounts of the deacetyl material and the acryloyl material which are the decomposition products of colforsin hydrochloride were determined. The produced amounts were measured as the ratios of the area of deacetyl compound and acryloyl compound to the total area of colforsin hydrochloride, deacetyl compound and acryloyl compound by a liquid chromatographic method. The results are shown in Table 13.

TABLE 13

| | Storage stability | | | |
| --- | --- | --- | --- | --- |
| | Initial | | After 21 days of storage | |
| Specimen | Deacetyl compound | Acryloyl compound | Deacetyl compound | Acryloyl compound |
| Control | 0.28% | 0.00% | 1.30% | 0.21% |
| Example 4 | 0.28% | 0.00% | 0.35% | 0.00% |
| Example 5 | 0.21% | 0.00% | 0.25% | 0.00% |
| Example 6 | 0.17% | 0.03% | 0.23% | 0.03% |
| Example 11 | 0.09% | 0.00% | 0.21%* | 0.10%* |

*Kept in storage for 28 days.

INDUSTRIAL APPLICABILITY

The oral preparation of the present invention has excellent storage stability. Also, the process of the present invention enables to obtain the pharmaceutical preparations with excellent storage stability.

What is claimed is:

1. An oral preparation prepared by a wet granulation method and comprising a salt of a forskolin derivative as a pharmaceutically active ingredient, and an alkali metal halide.

2. An oral preparation according to claim 1, wherein the salt of a forskolin derivative is a salt of a forskolin derivative represented by the following formula (1):

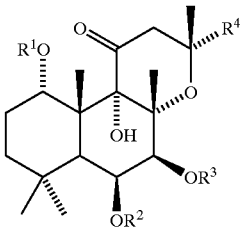

(1)

wherein $R^1$ is a hydrogen atom, $R^4$ is a vinyl group, an ethyl group or a cyclopropyl group, and one of $R^2$ and $R^3$ represents a partial structural formula $—CO(CH_2)mNR^5R^6$ wherein $R^5$ and $R^6$ are a hydrogen atom or a lower alkyl group, or they are combined to represent a lower alkylene group which may contain an oxygen atom or a nitrogen atom in its bonding chain, and m is an integer of 1 to 5, and the other is a hydrogen atom or a partial structural formula $—CO(CH_2)nX$ wherein X is a hydrogen atom or a group represented by the formula $—NR^7R^8$ wherein $R^7$ and $R^8$ are a hydrogen atom or a lower alkyl group, or they are combined to represent a lower alkylene group which may contain an oxygen atom or a nitrogen atom in the bonding chain, and n is an integer of 1 to 5.

3. An oral preparation according to claim 1, wherein the salt of a forskolin derivative is colforsin dapropate hydrochloride.

4. An oral preparation according to claim 1, wherein the alkali metal halide is sodium chloride or potassium chloride.

5. An oral preparation according to claim 1 or 2, wherein an alkali metal halide is contained in an amount of 0.1 to 26 parts by weight per one part by weight of a salt of a forskolin derivative.

6. An oral preparation according to claim 1, wherein an alkali metal halide is contained in an amount of 0.25 to 10 parts by weight per one part by weight of a salt of a forskolin derivative.

7. An oral preparation according to claim 1 or 2, wherein a pharmaceutical adjuvant or adjuvants are contained in an amount of 10 to 500 parts by weight per one part by weight of a salt of a forskolin derivative.

8. An oral preparation prepared by a wet granulation method and comprising:
   a salt of a forskolin derivative as a pharmaceutically active ingredient: 0.01–26 wt %
   an alkali metal halide: 0.05–22 wt %
   a pharmaceutical adjuvant or adjuvants: 52–99.9 wt %
   based on the whole preparation.

9. An oral preparation prepared by a wet granulation method and comprising:

| | |
| --- | --- |
| a salt of a forskolin derivative as a pharmaceutically active ingredient: | 0.03–13 wt % |
| sodium chloride or potassium chloride: | 0.25–11 wt % |
| a pharmaceutical adjuvant or adjuvants: | 76–99.7 wt % | based on the whole preparation.

10. An oral preparation according to claim 8 or 9, wherein the salt of a forskolin derivative is colforsin dapropate hydrochloride.

11. A process for producing a pharmaceutical preparation of a salt of a forskolin derivative with improved storage stability, said process comprising wet granulating a mixture of an aqueous solution of an alkali metal halide, said salt of a forskolin derivative and a pharmaceutical adjuvant or adjuvants.

12. A process for producing a pharmaceutical preparation of a salt of a forskolin derivative with improved storage stability, said process comprising mixing a solid alkali metal halide said salt of a forskolin derivative, and a pharmaceutical adjuvant or adjuvants, and wet granulating the mixture.

13. The process according to claim 11 or 12, wherein the salt of a forskolin derivative is colforsin dapropate hydrochloride.

14. The process according to claim 11 or 12, wherein the alkali metal halide is sodium chloride or potassium chloride.

15. The process according to claim 11 or 12, wherein a pharmaceutical adjuvant or adjuvants and an alkali metal halide are used in amounts of 10 to 500 parts by weight and 0.1 to 26 parts by weight, respectively, per one part by weight of the salt of the forskolin derivative.

16. The process according to claim 11 or 12, wherein a pharmaceutical adjuvant or adjuvants and an alkali metal halide are used in amounts of 10 to 500 parts by weight and 0.25 to 10 parts by weight, respectively, per one part by weight of the salt of a forskolin derivative.

17. The process according to claim 11, wherein the concentration of the alkali metal halide in its aqueous solution is from 1% by weight to the concentration of saturated solution.

18. The process according to claim 11, wherein the concentration of the alkali metal halide in its aqueous solution is from 5% by weight to the concentration of a saturated solution.

19. The process according to claim 12, wherein the solid alkali metal halide is powder type.

* * * * *

UNITED STATES PATENT AND TRADEMARK OFFICE
CERTIFICATE OF CORRECTION

PATENT NO. : 6,475,525 B1
DATED : November 5, 2002
INVENTOR(S) : Komuro et al.

It is certified that error appears in the above-identified patent and that said Letters Patent is hereby corrected as shown below:

<u>Title page,</u>
Please delete: "[30] Foreign Application Priority Data
  Sept. 20, 1996 (JP) 8-269168
  Aug. 29, 1997 (JP) 9-247533"

Signed and Sealed this

Twenty-ninth Day of April, 2003

JAMES E. ROGAN
*Director of the United States Patent and Trademark Office*